United States Patent [19]

Heuer et al.

[11] Patent Number: 5,675,032
[45] Date of Patent: Oct. 7, 1997

[54] PROCESS FOR THE PREPARATION OF SPECIFIC POLYETHYLENE GLYCOL DI (2-(4-CHLORO-2-METHYLPHENOXY)-PROPIONIC ACID ESTER MIXTURES

[75] Inventors: Lutz Heuer; Heinz-Joachim Rother; Volker Glock, all of Krefeld, Germany

[73] Assignee: Bayer Aktiengesellschaft, Leverkusen, Germany

[21] Appl. No.: 416,412

[22] Filed: Apr. 4, 1995

[30] Foreign Application Priority Data

Apr. 11, 1994 [DE] Germany .................... 44 12 330.2

[51] Int. Cl.⁶ .................................................. C07L 69/76
[52] U.S. Cl. .................................................. 560/62; 504/317
[58] Field of Search ................................ 560/62; 504/317

[56] References Cited

FOREIGN PATENT DOCUMENTS 0032631  7/1981  European Pat. Off. .

OTHER PUBLICATIONS

CA 91: 205517 (1979).

*Primary Examiner*—Paul J. Killos
*Attorney, Agent, or Firm*—Sprung Kramer Schaefer & Briscoe

[57] ABSTRACT

The present invention relates to an-economically and ecologically advantageous process, which is easy to carry out, for the preparation of specific polyethylene glycol diesters of 2-(4-chloro-2-methylphenoxy)-propionic acid, and to the substance mixture obtainable by this process and the use thereof as a root penetration inhibitor in building materials and insulating compositions, such as, for example, bitumen.

14 Claims, No Drawings

PROCESS FOR THE PREPARATION OF SPECIFIC POLYETHYLENE GLYCOL DI (2-(4-CHLORO-2-METHYLPHENOXY)- PROPIONIC ACID ESTER MIXTURES

The present invention relates to an economically and ecologically advantageous process, which is easy to carry out, for the preparation of specific polyethylene glycol diesters of 2-(4-chloro-2-methylphenoxy)-propionic acid (MCPP), and to the substance mixture obtainable by this process and the use thereof as a root penetration inhibitor in building materials and insulating compositions, such as, for example, bitumen.

The growth of roots through building materials leads to undesirable damage to the material. Plastic materials in particular, such as sealing compositions, roof sheathing and also asphalt can be destroyed by plant roots. The penetration of roots into seals of sewers and drains, into flat roof coverings and into bitumen insulations of pipelines and bridge and hydraulic constructions and the growth of roots into and through minor bitumen roads are generally known problems. Leaks, corrosion and damage to buildings, road and pipelines may be the consequence.

To prevent this damage, for example, F. Hegemann, Abiogene Bitumen-additive [Abiogenic bitumen additives], Bitumen-Teere-Asphalte-Peche 24, 105, (1973) describes addition of root-repellent active compounds to building materials.

Polyglycol esters of 2-(4-chloro-2-methylphenoxy)-propionic acid (called polyesters of MCPP acid in the following), for example, are known as active compounds from DE-1 196 115.

To prepare the polyesters of MCPP acid, polyglycols of average molecular weights 200 to 2.000 are reacted here with MCPP acid. The polyglycols are employed here in their molecular weight distribution obtained according to their preparation.

It is also known that the ethylene glycol, diethylene glycol and triethylene glycol esters and polyethylene glycol esters of MCPP acid can be used as herbicides. They are prepared by elimination of water by means of a catalyst (sulphuric acid) and entraining agent (benzene) and using a water separator. Working up requires various extraction and neutralization steps to remove the acid catalyst, and an expensive distillation ($\leq 0.5$ torr, $\geq 250°$ C). The yield here is in general 83 to 92 % of theory. The residue which remains contains a high content of MCPP acid, which must be separated off and disposed of by an expensive route, since it should not enter the waste water because of its high AOX content.

It is furthermore known from the literature that polyethylene glycols in general are in the form of mixtures of homologous (poly)-ethylene glycols having a high content of ethylene glycol. Ethylene glycol itself is having the highest vapour pressure and therefore the highest volatility because of its low boiling point. Since this also applies to the (poly)-ethylene glycol mono- and di-MCPP esters, a noticeable amount of product/starting material is lost during preparation by the customary processes. Furthermore, this volatile content causes a nuisance to the user during use of the MCPP acid polyesters thus prepared, for example during incorporation into hot bitumen mixtures.

It is also known that diethylene glycol (in general a substantial constituent of polyethylene glycols) forms dioxane under the influence of acid (H. Beyer, Lehrbuch der organischen Chemie [Textbook of organic chemistry], 18th edition. Hirzel Verlag, Stuttgart 1978, page 260). As a highly volatile component, dioxane is also discharged from the reaction mixture during preparation by the customary processes, and requires particular attention, since it readily forms explosive air/ether mixtures. The discharge of starting material furthermore reduces the yield.

To eliminate all of these disadvantages, a new process has been developed for the preparation of polyesters, in particular polyethylene glycol esters of MCPP acid.

The object of the invention was therefore to develop a process for the preparation of polyesters of MCPP acid which can be prepared rapidly and in a very good yield without the formation of dioxane or other highly volatile components. The biological expectations of inhibition of root penetration of, for example, bitumen furthermore were to be met in full or even exceeded.

It has now been found, surprisingly, that if a mixture of polyethylene glycols which has a molecular weight distribution $\overline{M}$ of 170 to 230 and is low in mono- and diethylene glycol is used instead of the known polyglycol mixtures, an increased yield coupled with a simultaneously increased biological action is observed.

The application therefore relates to a process for the preparation of polyethylene glycol esters of 2-(4-chloro-2-methylphenoxy)-propionic acid by reaction of polyethylene glycols with 2-(4-chloro-2-methyl-phenoxy)propionic acid, characterized in that the reaction is carried out with a mixture of polyethylene glycols having a molecular weight distribution ($\overline{M}$) of 170 to 230 and which is low in mono- and diethylene glycol, at temperatures of 155° to 195° C.

The mixture of polyethylene glycols of the required composition and molecular weight distribution is provided, for example, by mixing the particular pure ethylene glycol components or by mixing pure components with mixtures of various ethylene glycols or by mixing various mixtures of ethylene glycols. Polyethylene glycol mixtures of the following composition are preferred:

<0.1% by weight of monoethylene glycol (ME)

<0.1% by weight of diethylene glycol (DE)

5–40 % by weight of triethylene glycol (TRI)

30–80 % by weight of tetraethylene glycol (Tetra)

5–30 % by weight of pentaethylene glycol (PE)

0.1–10 % by weight of higher ethylene glycols (remainder).

Particularly preferred polyethylene glycol mixtures are those of the composition:

<0.05 % by weight of Me

<0.08 % by weight of DE

10–35 % by weight of TRI

35–75 % by weight of Tetra

10–25 % by weight of PE 0.5–8 % by weight of remainder.

Especially preferred polyethylene glycol mixtures are those of the composition:

<0.01% by weight of ME

<0.05 % by weight of DE

15–30 % by weight of TRI

48–70 % by weight of Tetra

12–22 % by weight of PE

1–7 % by weight of remainder.

The individual components of these compositions in each case add up to a total of 100 %.

The MCPP acid used for the reaction is that such as is commercially obtainable or, if appropriate, has been freed from residual water by heating at 100°–140° C.

In the process according to the invention, the polyethylene glycol mixture is introduced, preferably in an amount of 95–120 % by weight of theory, based on the required formation of the diester with the MCPP acid, into a reaction vessel containing the MCPP acid, preferably already heated to 155°–195° C. After 10 to 120 minutes, the pressure in the reaction vessel is reduced to preferably 50 to 1 mbar and the mixture is kept at this temperature and pressure for 15 to 45 hours.

The process according to the invention is preferably carried out at temperatures of 165°–190° C., in particular 170°–190° C. The pressure is preferably kept at 30 to 2, in particular 25 to 3 mbar, during the process.

The reaction has in general ended after 20–35 or, respectively, 22–30 hours at these temperatures and pressures.

Reaction vessels which are used are the generally customary, preferably enamelled systems. The process can also be carried out continuously, depending on the system, in which case the individual reaction components can be added simultaneously or in any desired sequence.

The application also relates to the product obtainable by the process according to the invention, which is distinguished by significantly improved properties compared with the known polyesters of MCPP acid.

The product obtainable thus has, for example, a reduced vapour pressure, which is advantageous in respect of industrial hygiene during use of the product. Furthermore, surprisingly, an increase in the biological, that is to say root-repellent action has been observed. The tolerability with adjacent planted areas was also improved.

The polyethylene glycol esters obtainable by the process according to the invention are used for protecting structures, such as, for example, sewers, pipelines, houses, roofs, roads, seals and bridge and hydraulic structures against roots growing in and through.

The polyethylene glycol esters according to the invention are applied directly to the structures, for example in the form of formulations, such as, for example, bitumen, coaltar pitches or paints, or are preferably added to the building materials, such as, for example, insulating and sealing compositions, roofing webs, cement and the like.

The content of active compound in the building materials or formulations here is 0.01 to 20 % by weight, preferably 0.01 to 5 % by weight, particularly preferably 0.3 to 2 % by weight.

Summarizing, it may be said that a new process has been found for the preparation of polyesters of MCPP acid, which is distinguished by the fact that it provides a polyester mixture in a short time, yields of ≧95 %, usually ≧98 %, being found in principle. Furthermore, compared with the prior art, further working up steps are eliminated, since a high conversion is achieved. In addition, surprisingly, the organic constituents discharged with the water formed are reduced to a minimum due to the use of a polyethylene mixture, to be prepared by mixing if appropriate, having an $\overline{M}$ of between 170 and 230, which offers ecological and economic advantages. This latter fact is particularly surprising, since it is not to be expected that the organic load in the waste water can be reduced by using similar polyethylene glycols having molecular weights of $\overline{M}\pm 200$.

The product obtainable by this process, moreover, is distinguished by significantly improved properties.

The use concentrations of the product with respect to the MCPP acid content are also lower, and the long-term action is improved.

The following examples serve to illustrate the invention.

STARTING MIXTURES

Starting glycol mixture I, polyethylene glycol 200 from Fluka for comparison examples 1 and 3

| Monoethylene glycol | 0.885% by weight |
|---|---|
| Diethylene glycol | 4.371% by weight |
| Triethylene glycol | 14.534% by weight |
| Tetraethylene glycol | 38.201% by weight |
| Pentaethylene glycol | 28.788% by weight |
| Hexaethylene glycol | 13.220% by weight |

Starting glycol mixtures II, polyethylene glycol, $\overline{M}\approx 200$ for examples 2 and 4 according to the invention

| Monoethylene glycol | 0.003% by weight |
|---|---|
| Diethylene glycol | 0.014% by weight |
| Triethylene glycol | 15.637% by weight |
| Tetraethylene glycol | 61.264% by weight |
| Pentaethylene glycol | 20.954% by weight |
| Hexaethylene glycol | 2.115% by weight |

EXAMPLE 1

7,450 g of MCPP acid are heated to 170° C.±5° C. in a 10 l reaction vessel and 3,088 g of glycol mixture I are added. After 30 minutes, the pressure is reduced to 3 to 8 mbar and the mixture is kept at 190° C.±5° C. for 30 hours.

After cooling 9,748 g of a dark oil are obtained.

EXAMPLE 2

7,450 g of MCPP acid are heated to 170° C.±5° C. in a 10 l reaction vessel and 3,423 g of glycol mixture II are added. After 30 minutes, the pressure is reduced to 3 to 8 mbar and the mixture is kept at 190° C.±5° C. for 9 hours 30 minutes.

After cooling, 10,061 g of a dark oil are obtained.

TABLE 1

HPLC Analysis of Examples 1 and 2

| Component | Example 2 (% by weight) -according to the invention- | Example 1 (% by weight) |
|---|---|---|
| 4-Chloro-2-methylphenol | 0.64 | 0.12 |
| MCPP acid | 1.6 | 4.7 |
| Diethylene glycol monoester | — | ≦0.1 |
| Triethylene glycol monoester | 0.92 | 0.12 |
| Tetraethylene glycol monoester | 2.4 | 0.25 |
| Pentaethylene glycol monoester | 0.96 | 0.25 |
| Monoethylene glycol diester | 0.52 | 2.1 |
| Diethylene glycol diester | 0.7 | 9.7 |
| Triethylene glycol diester | 20.6 | 23.8 |
| Tetraethylene glycol diester | 48.8 | 25.4 |
| Pentaethylene glycol diester | 18.1 | 17.0 |
| Hexaethylene glycol diester | 2.1 | 8.8 |
| Others | 3.12 | 7.69 |
| | 100.5 | 100.0 |

EXAMPLE 3

7,450 g of MCPP acid and 3,210 g of glycol mixture I are combined after the MCPP acid has been heated to 180° C.±5° C., and the mixture is kept at 190° C.±5° C. under 4–6 mbar for 24 hours 30 minutes.

After cooling, 9,966 g of a dark oil and 676 g of a volatile phase which has condensed off are obtained.

EXAMPLE 4

7.368 g of MCPP acid and 3.432 g of glycol mixture II are combined after the MCPP acid has been heated to 180° C.±5° C., and the mixture is kept at 190°–200° C. under 4–6 mbar for 24 hours 15 minutes.

After cooling, 9.995 g of a dark oil and 581 g of a volatile phase which has condensed off are obtained.

EXAMPLE 5

The oils from Example 1 and 2 are tested for their action on inhibition of root penetration in accordance with DIN 4062 and are found to be equally good and highly active.

TABLE 2

| Number of root inwards growth/number of plants (at a 0.5% active compound content) | Effective action in % |
|---|---|
| Example 1  0.40 | 60 |
| Example 2  0.13 | 87 |

Furthermore, when the active compound according to Examples 1 and 3 is employed, damage to the plants is observed on some plants, which is not observed when the active compounds according to Examples 2 and 4 are employed.

We claim:

1. Process for the preparation of polyethylene glycol esters of 2-(4-chloro-2-methylphenoxy)-propionic acid by reaction of polyethylene glycols with 2-(4-chloro-2-methylphenoxy)propionic acid, characterized in that the reaction is carried out with a mixture of polyethylene glycols having a molecular weight distribution of 170 to 230 and which mixture contains less than 0.1% by weight mono- and less than 0.1% by weight diethylene glycol, at temperatures of 155°–195° C.

2. Process according to claim 1, characterized in that the reaction is carried out with a polyethylene glycol mixture of <0.1% by weight of monoethylene glycol, <0.1% by weight of diethylene glycol, 5–40 % by weight of triethylene glycol, 30–80 % by weight of tetraethylene glycol, 5–30% by weight of pentaethylene glycol and 0.1–10 % by weight of higher ethylene glycols.

3. Process according to claim 1, characterized in that the reaction is carried out under reduced pressure.

4. Process according to claim 1, characterized in that the reaction is carried out at temperatures of 165–190° C. under a pressure of 30 to 2 mbar.

5. Process according to claim 1, characterized in that the reaction is carried out at temperatures of 170–190° C. under a pressure of 25 to 3 mbar.

6. The polyethylene glycol esters of 2-(4-chloro-2-methylphenoxy)-propionic acid obtainable by the process according to claim 1.

7. In the protection of a structure against penetration by roots growing therethrough by incorporating a root-repellent material in the structure, the improvement wherein such material is an ester according to claim 6.

8. A building material containing a root-repellent amount of an ester according to claim 6.

9. The process according to claim 1, wherein the polyethylene glycol mixture comprises:

<0.05% by weight of monoethylene glycol;

<0.08% by weight of diethylene glycol;

10–35% by weight of triethylene glycol;

35–75% by weight of tetraethylene glycol;

10–25% by weight of pentaethylene glycol; and 0.5–8% by weight of higher ethylene glycols wherein the individual components add up to 100%.

10. The process according to claim 1, wherein the polyethylene glycol mixture comprises:

<0.01% by weight of monoethylene glycol;

<0.05% by weight of diethylene glycol;

15–30% by weight of triethylene glycol;

48–70% by weight of tetraethylene glycol;

12–22% by weight of pentaethylene glycol;

1–7% by weight of higher ethylene glycol; and wherein the individual components add up to 100%.

11. The process according to claim 1, wherein the polyethylene glycol mixture comprises:

0.003% by weight of monoethylene glycol;

0.014% by weight of diethylene glycol;

15.637% by weight of triethylene glycol;

61.264% by weight of tetraethylene glycol;

20.954% by weight of pentaethylene glycol; and 2.115% by weight of hexaethylene glycol.

12. The mixture of polyethylene glycol esters of MCPP which is obtainable by the process of claim 9.

13. The mixture of polyethylene glycol esters of MCPP which is obtainable by the process of claim 10.

14. The mixture of polyethylene glycol esters of MCPP which is obtainable by the process of claim 11.

* * * * *